(12) United States Patent
Figueredo Torres

(10) Patent No.: US 6,837,707 B2
(45) Date of Patent: Jan. 4, 2005

(54) DOUBLE DENTAL MIRROR

(76) Inventor: Josefina Figueredo Torres, 6401 N. Blossom Ave., Tampa, FL (US) 33614

( * ) Notice: Subject to any disclaimer, the term of this patent is extended or adjusted under 35 U.S.C. 154(b) by 0 days.

(21) Appl. No.: 10/283,581

(22) Filed: Oct. 30, 2002

(65) Prior Publication Data
US 2004/0086828 A1 May 6, 2004

(51) Int. Cl.[7] ................................... A61C 3/00
(52) U.S. Cl. ........................................ 433/31
(58) Field of Search ................ 433/31, 30, 3, 433/29, 80, 141; 359/882; 600/247, 248, 189; 132/309; 248/477, 476; 24/31, 31 B, 33 M; 403/108, 107

(56) References Cited

U.S. PATENT DOCUMENTS

| | | | | |
|---|---|---|---|---|
| 965,079 A | * | 7/1910 | Caswell | 433/30 |
| 1,540,409 A | * | 6/1925 | McCray | 359/855 |
| 1,925,981 A | * | 9/1933 | Hopkins | 433/31 |
| 2,436,040 A | * | 2/1948 | Friedman | 433/30 |
| 3,151,395 A | * | 10/1964 | Moniot | 433/30 |
| 3,300,859 A | * | 1/1967 | Sanden | 433/30 |
| 4,512,635 A | * | 4/1985 | Melde | 359/882 |
| 5,203,694 A | * | 4/1993 | Klein | 433/5 |
| 6,619,954 B2 | * | 9/2003 | Cheney et al. | 433/29 |

* cited by examiner

*Primary Examiner*—Melba Bumgarner
(74) *Attorney, Agent, or Firm*—Pendorf & Cutliff

(57) ABSTRACT

A double dental mirror to provide a multi-angular view of a working area, the double dental mirror comprising: a first mirror; a second mirror; and a bridge section. The bridge section forms at least one of an angle and an arch. The configuration of the dental mirror provides the dental practitioner with multiple views of the working area, and at the same time, provides an enlargement of the working area by isolating the tongue and cheeks from the working area.

17 Claims, 2 Drawing Sheets

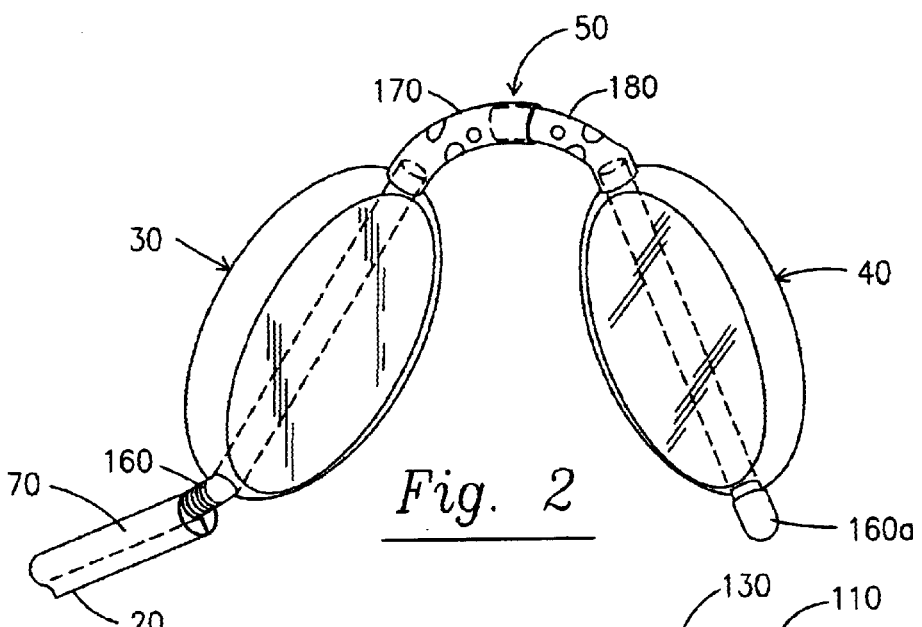
Fig. 2
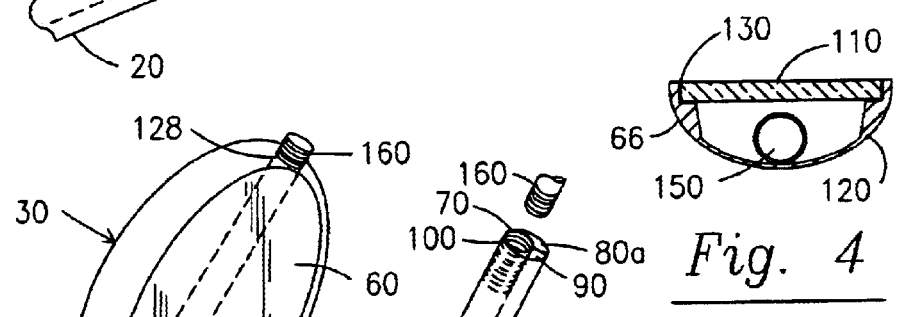
Fig. 3
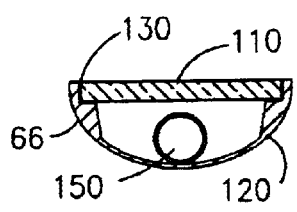
Fig. 3a
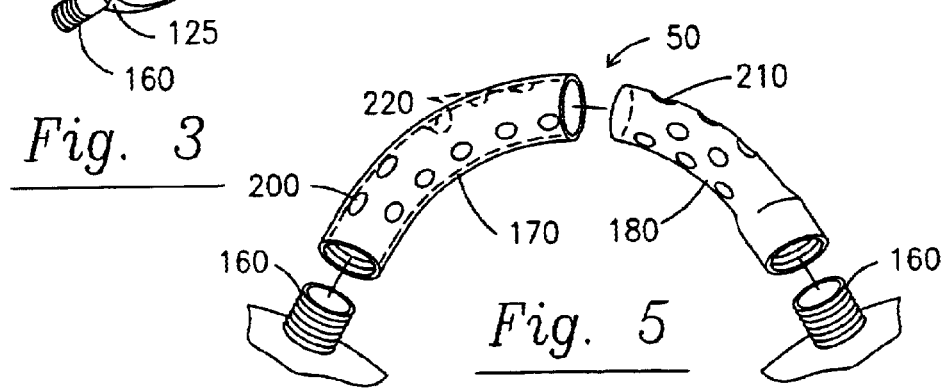
Fig. 4
Fig. 5

DOUBLE DENTAL MIRROR

BACKGROUND OF THE INVENTION

1. Field of the Invention

The present invention concerns a dental mirror, and more specifically, a double dental mirror that provides the dental practitioner with a multi-angular view of the working area and at the same time, retracts the tongue and cheeks, increasing the operative field around the working area.

2. Description of the Prior Art

Dental mirrors have long been used to assist dental practitioners in performing diagnostic and treatment procedures. The stereotypical dental mirror has a handle with a small mirror affixed at an angle on the end of the handle so that it can be inserted into the patient's mouth for viewing inside the patient's mouth.

When the work is performed in the frontal part of the mouth, generally any mirror will suffice. But if the work is performed in the posterior part of the mouth, or the working area is hidden from the field of view of the dental practitioner, then a mirror that provides a multi-angular viewing, or a lateral view of the working area, is required.

The prior art shows several double dental mirrors having a pair of mirrors connected back to back. Unfortunately, these types of dental mirrors do not provide the dental practitioner with the multi-angular view required when working in the back part of the mouth. Also, these types of mirrors fail to show a lateral view of the working areas.

U.S. Pat. No. 6,068,379 entitled "Diamond Surface Mirror" to Kempf shows a dental mirror having two mirrors placed side by side.

While the dental mirror of the Kempt reference may be suitable for the particular purpose to which it is addressed, it would not be as suitable for the purpose of the present invention as hereafter described.

Even if the dental mirror shown in the Kempt reference provides the user with lateral mirrors, these dental mirrors cannot be used crossing over the dental arch because of the way that they are connected, and the way that the handle is connected to the mirrors. The two mirrors are positioned at an angle, thus the reflection of one of the mirrors has to be observed by looking at the other mirror.

During oral procedures, the dental practitioner also encounters many difficulties. One of the greatest difficulties is the small working space of the oral cavity; thus, increasing the size of the operative field has been one of the major concerns of the dental practitioner.

Another difficulty is that patients have problems in keeping their tongues and cheeks from entering or obstructing the working area. Further, keeping the work surface clean and dry is very difficult.

In order to overcome these difficulties, the prior art provides devices for isolating the working area and for keeping the work area clean. But unfortunately, these devices have some disadvantages. First, to isolate the working area, the prior art devices retract the tongue of the patient by depressing the tongue. Tongue depression can be quite uncomfortable for the patient and is only a marginally effective technique since a patient's tongue can slip from beneath the depressor. Second, the devices of the prior art, in some fashion or another, obstruct the operative field in which a dental practitioner must work. Third, the prior art devices only isolate the tongue from the working area, but do not provide isolation of the cheeks from the working area or vice versa.

Thus, none of the prior art fully maximizes the size of the operative field.

There is need, therefore, for an oral device which provides an optimal size to the operative field by retracting both the tongue and the cheek adjacent to the working area, maintains a clear operative field by creating no obstructions, and enables efficient simultaneous evacuation of saliva, aerosol, and debris from the oral cavity.

SUMMARY OF THE INVENTION

A primary object of the present invention is to provide a double mirror that will overcome the shortcomings of the prior art double dental mirror.

It is yet another object of the present invention to provide a double dental mirror that provides the dental practitioner with the multi-angular view required when working in the back part of the mouth.

It is yet another object of the present invention to provide a double dental mirror that provides the dental practitioner with a lateral view of the working areas.

It is yet another object of the present invention to provide a double dental mirror that provides an optimal size to the operative field by retracting both the tongue and the cheek from the working area.

It is yet another object of the present invention to provide a double dental mirror that maintains a clear operative working area by creating no obstructions, and enables efficient simultaneous evacuation of saliva, aerosol, and debris from the oral cavity.

It is yet another object of the present invention to provide a double dental mirror which can be easily inserted into the oral cavity.

It is yet another object of the present invention to provide a double dental mirror which can be fabricated inexpensively.

It is yet a further object of the present invention to provide a dental mirror, which is easy to use, causes no, or minimal, patient discomfort, and relieves the dental practitioner from the need to reposition the dental mirror during a dental procedure.

Other objects and advantages of this invention will become more fully apparent as this description proceeds; reference being made to the accompanying drawings and appended claims.

Briefly stated, the present invention contemplates a double dental mirror to provide multi-angular view of a working area, the double dental mirror comprising:
a first mirror;
a second mirror; and
a bridge section;
wherein the bridge section forms at least one of an angle and an arch.

The double dental mirror of the present invention is adapted to be used in connection with a handle comprising a first end, a second end, a length, and a longitudinal passage extending through the length of the handle. The longitudinal passage is adapted to carry suction means, lights means, water line and/or airline.

Further, the double dental mirror of the present invention is used in conjunction with a bite block.

The configuration of the present invention provides the dental practitioner with a dental mirror that shows multiple views of the working area, and at the same time, provides an enlargement of the working area by isolating the tongue and cheeks from the working area.

In order to fix the different size oral cavities, the present invention includes a mechanism for adjustably setting the mirrors into one or more of a plurality of angles. The mechanism consists of a plurality of recesses and protrusions that interconnect with each other in order to adjust the length of the bridge and the angle of the mirrors. Further, the threaded shank helps adjusting the height of the mirror, allowing the practitioner to insert the mirror in small oral cavities.

The foregoing has outlined the more pertinent and important features of the present invention in order that the detailed description of the invention that follows may be better understood, and the present contributions to the art may be more fully appreciated. Additional features of the present invention will be described hereinafter, which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWING FIGURES

The figures in the drawings are briefly described as follows:

FIG. 2 shows an enlargement view of the double dental mirror, according to the present invention.

FIG. 3 shows an enlargement view showing one of the mirrors of the double dental mirror, according to the present invention.

FIG. 3a shows an enlargement view of the handle and mirror connection of FIG. 1.

FIG. 4 shows a cross sectional view of the mirror of FIG. 3.

FIG. 5 shows an enlargement view showing the bridge section of the double dental mirror, according to the present invention.

FIG. 6 shows the dental mirror of the present invention use in conjunction with a bite block.

DETAILED DESCRIPTION OF THE INVENTION

Figure 1:
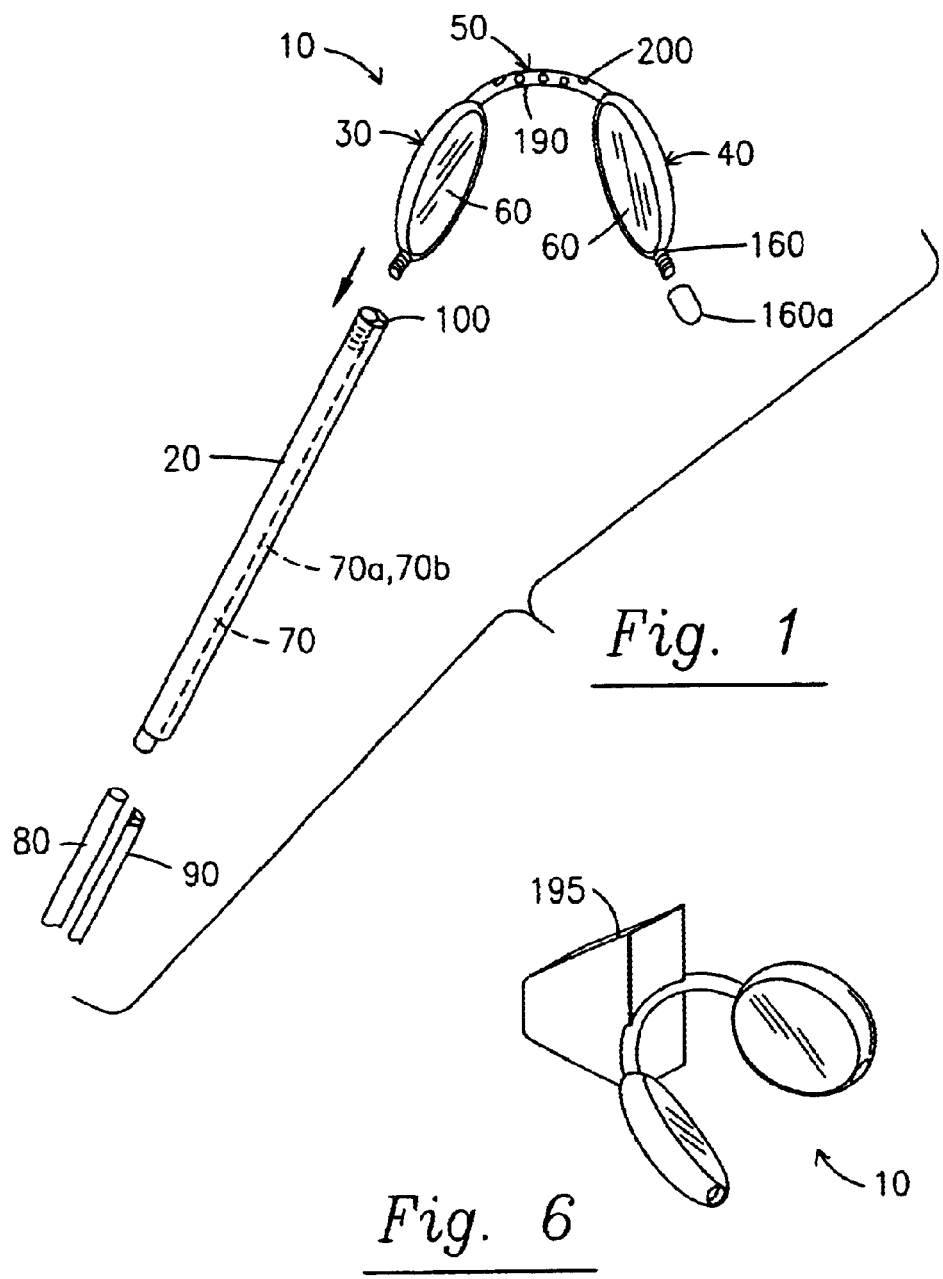
FIG. 1 shows a front view of the double dental mirror, including a handle, according to the present invention.

Turning now descriptively to the drawings, in which similar reference characters denote similar elements throughout the several views, FIG. 1 illustrates a double dental mirror 10 in connection with a handle portion 20. The double dental mirror comprises a first mirror 30 a second mirror 40 and a bridge section 50.

Handle

The handle 20 is made of any suitable material that can withstand the sterilization process. Preferably, the present invention contemplates the use of plastic material or, in the alternative, a metal such as stainless steel. The handle 20 includes a coupling means 100 at both ends of the handle.

In the first embodiment of the present invention, the handle includes a longitudinal passage 70 extending through the length of the handle. The longitudinal passage 70 is adapted to carry suction means 80 for draining water, saliva and debris from the patient's mouth.

The present invention also contemplates illuminating the dental mirror and/or the working area by inserting light means 90 through the longitudinal passage 70a and 70b.

Further, the present invention contemplates passing through the longitudinal passage 70b a water line and an air line for washing and drying the mirror and/or working areas.

In the second embodiment of the present invention, the handle does not include the longitudinal passage, thus the dental mirror does not have aspirating capability. The simple and economical design of the dental mirror according to this embodiment, provides the dental practitioner with the option of discarding the mirror after each use.

Mirrors

The mirrors 30, 40 of the present invention include a thin, glass disc 110 having a reflective surface 60. The glass disc 110 is held in place inside a housing 120 by using any fastening means 130 such as clips, clamps, rubber bands, and glue.

FIG. 4 shows the housing 120 having an external convex shell with a concave interior and a step 66 where the glass disc 110 rests. The glass disc 110 is surrounded by a fastening means 130 such as a rubber band that allows the glass disc 110 to be inserted into the shell by pressure. This design facilities the replacement of the reflective surface by simple pulling the rubber band.

The rubber band is made of any material that can resist the sterilization process.

The housing 120 includes a first end 125, a second end 128, and an opening 150. The opening 150 is connected to the longitudinal passage 70 of the handle 20 to carry suction means 80 for draining water, saliva, and debris from the patient's mouth.

Each end 125, 128 of the housing 120 includes a hollow threaded shank 160 that extends outwardly or inwardly. The threaded shank 160 is attached to the housing by any suitable means, preferably molded into the end of the housing 120.

The threaded shank 160 of the end 128 is connected inside the bridge, thus the rotation of the mirror allows the mirror to be aligned with the bridge. This structure permits the insertion of the mirror into small oral cavities.

The threaded shank 160 of the end 125 and coupling means 100 of the handle can be engaged together so that they can be easily assembled and/or disassembled. A key advantage to this type of detachable mounting is that it allows one to easily interchange mirrors having different optical properties, which optimize the invention's usefulness and also allows the handle to be connected to any of the threaded shanks 160 of the mirrors.

The threaded shank 160 of the end 125 is designed to form an open angle between 90 to 180° with the longitudinal axis of the mirror. This design helps pushing the lips from outside, providing a better visibility of the working area.

The threads of the threaded shank 160 of the end 125 permit the double dental mirror to be unthreaded from the handle, thus the mirror can be used in conjunction with a bite block 195 without a handle.

When the threaded shank is not coupled to a handle, the present invention contemplates using a cap 160a to cover the threaded shank in order to avoid loosing the vacuum effect. The cap protects the patient from being scratched by the threaded shank. The cap 160a is made of any material that can resist the sterilization process such as rubber or metal.

The housing may be of any desirable shape, preferably round or oval-shape. Both shapes of the housing help to retract the tongue and cheeks away from the teeth within the oral cavity.

The dental mirror of the present invention does not push the tongue and cheeks from the working area, but rather serves a barrier to avoid that the tongue and cheeks interfere with the working area.

The size and shape of the mirrors create a barrier to the tongue and cheek entering the operative field.

Bridge

The two dental mirrors connect via a bridge 50. The bridge comprises a first section 170 and a second section 180 that interconnect to each other, which forms at least one of an angle and an arch.

Each section further comprises suction inlet apertures 200 through which saliva, fluid, and debris are evacuated from the oral cavity.

Each section 170, 180 also comprises a plurality of recesses 210 and protrusions 220 that interconnect with each other in order to adjust the length of the bridge and the angle of the mirrors. Further, each section includes internal or external threads to help in the connection with the threaded shank 160 outwardly or inwardly respectively.

The bridge 50 must be of a length sufficient to pass over the dental arch and/or rearward to a rearmost molar when positioned within the oral cavity, and preferably have a U-shape. This configuration provides that at least one suction inlet is adjacent to a rearmost molar tooth.

The planes of the mirrors are disposed in open angles from the bottom to the top and from the back to the front. For the purposes associated with this invention, however, the angles of the mirrors are set from between about 0° to about 180°, preferably 30–60°, most preferably 45°. It must be understood, however, that greater and lesser angles may also be pre-set.

The dental mirror of the present invention can be used in conjunction with a bite block 195 as can be seen in FIG. 6.

To use the dental mirror, according to the present invention, the dental practitioner grasps the dental mirror and inserts it into the patient's oral cavity so that the bridge is inserted first and is fitted crossing the dental arch or crossing the alveolar ridge. When in proper position, the bridge will be behind the rear most tooth, and/or crossing the dental arch or alveolar ridge, one of the mirrors will be on the cheek side of the oral cavity, and the other mirror will be on the lingual side of the oral cavity. Upon proper placement of the device, the mirrors exert opposing positional influence against the cheek and tongue, resulting in retraction of the tongue and cheek, thereby creating a clear operative field.

The present invention simultaneously increases the size of the operating field, decreases the amount of fluid in the oral cavity and gives the dental practitioner multi-angular views of the working area.

Additionally, the simple design of this device lends itself to fabrication with inexpensive, single-use materials that can be disposable.

None of the prior art dental mirrors provide an optical device that increases the lateral view of the operative field with minimum obstruction of the forward visual field, is inexpensive to manufacture, light in weight, easy to use, and extends the lateral view without loss of the front view.

While the principles of the invention have been made clear in the description, it will be immediately obvious to those skilled in the art many modifications of structure, arrangement, proportions, the elements, materials, and components used in the practice of the invention, and otherwise, which are particularly adapted for specific environments and operative requirements without departing from those principles.

The appended claims are intended to cover and embrace any and all such modifications, within the limits only of the true spirit and scope of the invention. This specification and the appended claims have been prepared in accordance with the applicable patent laws and the rules promulgated under the authority thereof.

What I claim is:

1. A double dental mirror to provide a multi-angular view of a working area, the double dental mirror comprising:

a first mirror;

a second mirror; and a bridge having a first section and a second section, wherein the first section and the second section interconnect to each other;

wherein the bridge sections form at least one of an angle and an arch; and wherein the first section comprises a plurality of recesses and protrusions and the second section comprises a plurality of recesses and protrusions, wherein the recesses of the first section interconnect with the protrusions of the second section and wherein the protrusions of the first section interconnect with the recesses of the second section.

2. A double dental mirror, according to claim 1, further comprising a handle comprising a first end, a second end, and a length.

3. A double dental mirror, according to claim 2, wherein the handle includes a coupling means at both ends of the handle.

4. A double dental mirror, according to claim 2, wherein the handle includes a longitudinal passage extending through the length of the handle, wherein the longitudinal passage is adapted to carry suction means for draining water, saliva and debris from the patient's mouth.

5. A double dental mirror, according to claim 4, wherein longitudinal passage is adapted to further carry a light means.

6. A double dental mirror, according to claim 4, wherein longitudinal passage further includes a water line and an air line for washing and drying at least one of the mirrors and working area.

7. A double dental mirror, according to claim 1, wherein each mirror includes a thin, glass disc having a reflective surface, wherein the glass disc is held in place inside a housing by using fastening means.

8. A double dental mirror, according to claim 7, wherein the housing includes an external convex shell having a concave interior and a step where the reflective surface rests.

9. A double dental mirror, according to claim 8, wherein the reflective surface is surrounded by a rubber band that allows the reflective surface to be locked into the shell by pressure.

10. A double dental mirror, according to claim 9, wherein the reflective surface is replaceable.

11. A double dental mirror, according to claim 8, wherein the housing further includes a first end, a second end, and an opening.

12. A double dental mirror, according to claim 11, wherein the opening is connected to a longitudinal passage of the handle, and wherein the opening is adapted to carry suction means, light means, water lines, and air lines.

13. A double dental mirror, according to claim 1, wherein both sections further comprise suction inlet apertures through which saliva, fluid, and debris are evacuated from the oral cavity.

14. A double dental mirror, according to claim 1, wherein the dental mirror is used in conjunction with a bite block.

15. A double dental mirror to provide a multi-angular view of a working area, the double dental mirror comprising:
- a first mirror;
- a second mirror;
- a bridge section;
- wherein the bridge section forms at least one of an angle or an arch;
- wherein each mirror includes a thin, glass disc having a reflective surface, wherein the glass disc is held in place inside a housing by using fastening means;
- wherein the housing includes an external convex shell having a concave interior and a step where the reflective surface rests;
- wherein the housing further includes a first end, a second end, and an opening;
- wherein each end of the housing includes a hollow threaded shank that extends outwardly or inwardly.

16. A double dental mirror, according to claim 15, wherein the threaded shank of the housing and coupling means of a handle engage together so that they can be easily assembled and/or disassembled.

17. A double dental mirror, according to claim 15, wherein the threaded shank forms an open angle between 90 to 180° with the mirror.

* * * * *